United States Patent [19]

Tsushima et al.

[11] Patent Number: 5,461,044
[45] Date of Patent: Oct. 24, 1995

[54] CEPHALOSPORIN DERIVATIVES

[75] Inventors: Masaki Tsushima; Katsuyoshi Iwamatsu; Atsushi Tamura; Seiji Shibahara, all of Yokohama, Japan

[73] Assignee: Meiji Seika Kaisha, Ltd., Japan

[21] Appl. No.: 369,274

[22] Filed: Jan. 5, 1995

Related U.S. Application Data

[63] Continuation of Ser. No. 925,035, Aug. 5, 1992, abandoned.

[30] Foreign Application Priority Data

Aug. 13, 1991 [JP] Japan ................. 3-226401

[51] Int. Cl.$^6$ ............ C07D 501/59; A61K 31/545
[52] U.S. Cl. ............................... 514/206; 540/227
[58] Field of Search ............... 540/227, 226; 514/206

[56] References Cited

U.S. PATENT DOCUMENTS

| | | | |
|---|---|---|---|
| 4,812,562 | 5/1989 | Watanabe et al. | 540/227 |
| 4,921,953 | 5/1990 | Yokoo et al. | 540/227 |
| 5,247,073 | 9/1993 | Temansky | 540/227 |

FOREIGN PATENT DOCUMENTS

| | | |
|---|---|---|
| 0009008 | 3/1980 | European Pat. Off. . |
| 0210078 | 1/1987 | European Pat. Off. . |
| 0432042 | 6/1991 | European Pat. Off. . |
| 0495584A | 2/1992 | European Pat. Off. . |

OTHER PUBLICATIONS

Chemical Abstracts vol. 118:233769 (1993).

*Primary Examiner*—Nicholas Rizzo
*Attorney, Agent, or Firm*—Lalos & Keegan

[57] ABSTRACT

As new antibacterial agent are provided cephalosporin derivatives having a general formula (I):

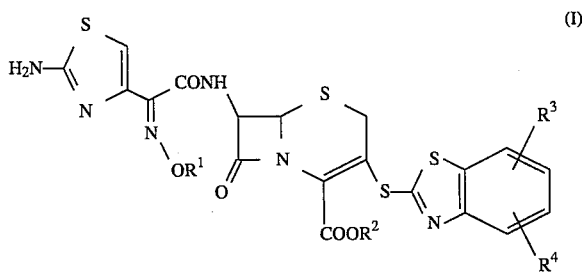

wherein $R^1$ is a hydrogen atom, a lower alkyl group or a substituted lower alkyl group, $R^2$ is a hydrogen atom or an ester-forming group easily cleavable by an esterase present in the digestive tracts, $R^3$ and $R^4$ may be the same and each is independently a hydrogen atom, a halogen atom, a lower alkyl group, a lower alkenyl group, hydroxyl group, amino group or a lower alkoxy group, and a pharmaceutically acceptable salt thereof.

The cephalosporin derivative of formula (I) is useful as an orally or injectably administrable cephalosporin derivative which exhibits in combination a high antibacterial activity and a favorable characteristic capable of giving a high concentration of this compound in blood when administered.

3 Claims, No Drawings

CEPHALOSPORIN DERIVATIVES

This is a continuation of copending application of Ser. No. 07/925,035 filed on Aug 5, 1992, now abandoned and which designated in the U.S.

SUMMARY OF THE INVENTION

This invention relates to new cephalosporin derivatives having a benzothiazolylthio group as the substituent at the 3-position of the cephem nucleus. More particularly, this invention relates to new cephalosporin derivatives having a high antibacterial activity and a favorable characteristic capable of giving a high concentration of this cephalosporin derivative in blood when administered to mammals. This invention further relates to a pharmaceutical, antibacterial composition comprising the cephalosporin derivative as active ingredient.

BACKGROUND OF THE INVENTION

A cephalosporin antibiotic has an excellent antibacterial activity and a low toxicity to mammals, and therefore it is an extremely effective medicine useful for the therapeutic treatment of bacterial infections in the mammals. In recent years, many cephalosporin derivatives having an aminothiazolylacetyl group at the 7-position of the cephem ring have been researched and developed, because they have a strong antibacterial activity and a stability to β-lactamase.

The so-called third-generation cephalosporin antibiotics represented by cefotaxime and cefmenoxime have the aminothiazolylacetyl group at the 7-position and are characterized by a high antibacterial activity and wide antibacterial spectra, and so they have been practically used in many countries of the world. However, some compounds amongst the third-generation cephalosporin antibiotics such as cefotaxime and cefmenoxime are not satisfactory in points of their antibacterial activity to *Pseudomonas aeruginosa* and methicillin-resistant *Staphylococcus aureus* which clinically provide some problems in the recent years. In particular, the methicillin-resistant *Staphylococcus aureus* brings about a serious bacterial infection, and nowadays it is desired to provide a novel cephalosporin antibiotic having an improved antibacterial activity to these resistant bacteria.

Incidentally, one of the present inventors and his colleague have earlier succeeded in synthetizing a new class of cephalosporin derivative of general formula (A):

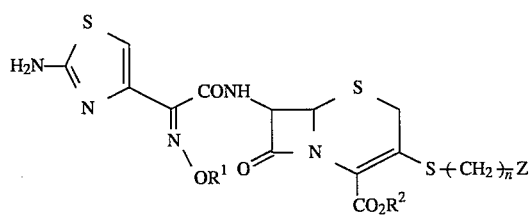

wherein $R^1$ is a hydrogen atom or a lower alkyl group, $R^2$ is a hydrogen atom or an ester-forming group capable of being cleaved easily with an esterase existing in the digestive tracts; n is an integer of zero or 1; Z is a saturated heterocyclic group containing one or two oxygen atoms as the hetero-atoms with or without one or more lower alkyl substituents, or a pharmaceutically acceptable salt thereof (U.S. patent application Ser. No. 623,215 filed Dec. 6, 1990, now U.S. Pat. No. 5,332,731 and European patent application publication No. 0 432 042 A2).

DETAILED DESCRIPTION OF THE INVENTION

In order to provide new cephalosporin derivatives which can meet the outstanding demands, we, the present inventors, have intensively researched. As a result, we have succeeded in synthesis of a novel cephalosporin derivative represented by the undermentioned general formula (I), and we have found that the new cephalosporin derivative of formula (I) has a combination of an excellent antibacterial activity and a favorable characteristic capable of giving a high concentration of this compound in blood upon its administration. In addition, it has been found that the compound of the general formula (I) may be given through any route of administration, including subcutaneous injection, intravenous injection and other injections as well as oral administration. The present invention has been completed on the basis of these findings.

According to the present invention, therefore, there is provided a new cephalosporin derivative represented by the general formula ( I )

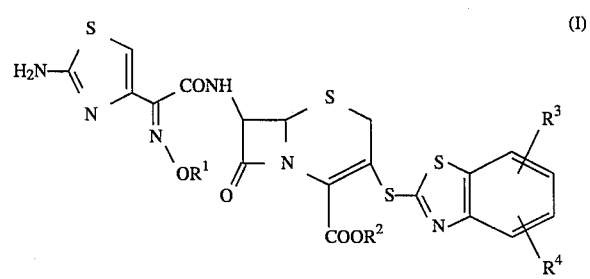

wherein $R^1$ is a hydrogen atom, a lower alkyl group or a substituted lower alkyl group, $R^2$ is a hydrogen atom or an ester-forming group easily cleavable by an esterase present in the digestive tracts, $R^3$ and $R^4$ may be the same and each is independently a hydrogen atom, a halogen atom, a lower alkyl group, a lower alkenyl group, hydroxyl group, amino group or a lower alkoxy group, and a pharmaceutically acceptable salt thereof.

In this specification, the lower alkyl group and an alkyl portion of the lower alkoxy group present in the compound of the general formula (I) means a straight or branched alkyl group having 4 or less carbon atoms. Furthermore, the halogen atom means a fluorine, chlorine, bromine or iodine atom, for example.

With the cephalosporin derivative of the general formula (I) where $R^1$ is a substituted lower alkyl group, such substituted lower alkyl group may preferably be a lower alkyl group having a carboxyl substituent or having a protected carboxyl substituent which may be, e.g., an lower alkoxycarbonyl group.

The ester-forming group represented by $R^2$ is such one that can easily be cleaved by hydrolysis with an esterase enzyme in vivo after the administration of the compound of formula (I). Examples of such ester-forming group include a 1-acyloxy-lower alkyl group, particularly a 1-lower alkanoyloxy-lower alkyl group, such as a pivaloyloxymethyl group, acetoxymethyl group and 1-acetoxyethyl group; a 1-alkoxycarbonyloxy-lower alkyl group such as 1-(ethoxycarbonyloxy)ethyl group and 1-(isopropoxycarbonyloxy)ethyl group; and (5-methyl-1,3-dioxoten-4-yl)methyl group.

A preferred embodiment of the cephalosporin derivative of the general formula (I) is such one in which $R^1$ is a hydrogen atom, $R^2$ is a hydrogen atom or an ester-forming group as mentioned above, and $R^3$ and $R^4$ are each a hydrogen atom.

A further preferred embodiment of the cephalosporin derivative of the formula (I) is such one in which $R^1$ is methyl or ethyl group, $R^2$ is a hydrogen atom or an ester-forming group as mentioned above, and $R^3$ and $R^4$ are each a hydrogen atom.

Another embodiment of the cephalosporin derivative of the formula (I) is such one in which $R^1$ is carboxymethyl group or carboxyethyl group, $R^2$ is a hydrogen atom or an ester-forming group as mentioned above, and $R^3$ and $R^4$ are each a hydrogen atom.

The ester-forming group for $R^2$ in the cephalosporin derivative of the formula (I) may preferably be selected from pivaloyloxymethyl group, acetoxymethyl group, 1-acetoxyethyl group, 1-(ethoxycarbonyloxy)ethyl group, 1-(isopropoxycarbonyloxy)ethyl group and (5-methyl-1,3-dioxolen-4-yl) methyl group.

Next, typical examples of the cephalosporin derivative of the general formula (I) according to this invention will be enumerated, but this invention should not be limited to these particular examples.

1. 7-[(Z)-2-(2-aminothiazol-4-yl)-2-methoxyiminoacetamido]-3-(benzothiazol-2-yl)thio-3-cephem-4-carboxylic acid
2. Pivaloyloxymethyl 7-[(Z)-2-(2-aminothiazol 4-yl)-2-methoxyiminoacetamido]-3-(benzothiazol-2-yl)thio 3-cephem-4-carboxylate
3. 7-[(Z)-2-(2-aminothiazol-4-yl)-2-hydroxyiminoacetamido]-3-(benzothiazol-2-yl)thio-3-cephem-4-carboxylic acid and its pivaloyloxymethyl ester
4. 7-[(Z)-2-(2-aminothiazol-4-yl)-2-carboxymethoxyiminoacetoamido]-3-(benzothiazol-2-yl)thio-3-cephem-4-carboxylic acid and its pivaloyloxymethyl ester The cephalosporin compound having the formula (I) according to this invention can be prepared by various production methods, but it is convenient to prepare the same in accordance with the production process (A) comprising the successive steps 1 to 5 depicted by the following reaction scheme. Production process (A):

Step 1

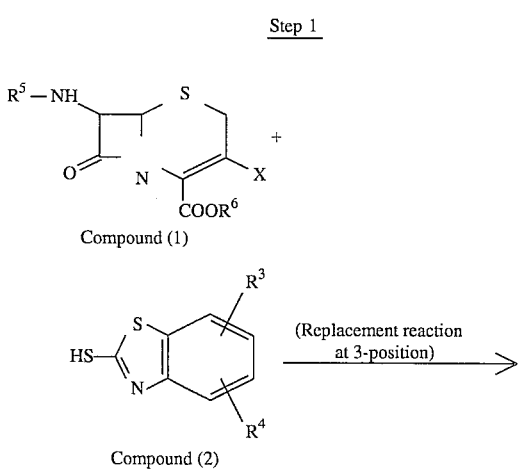

Compound (1)

Compound (2)

(Replacement reaction at 3-position)

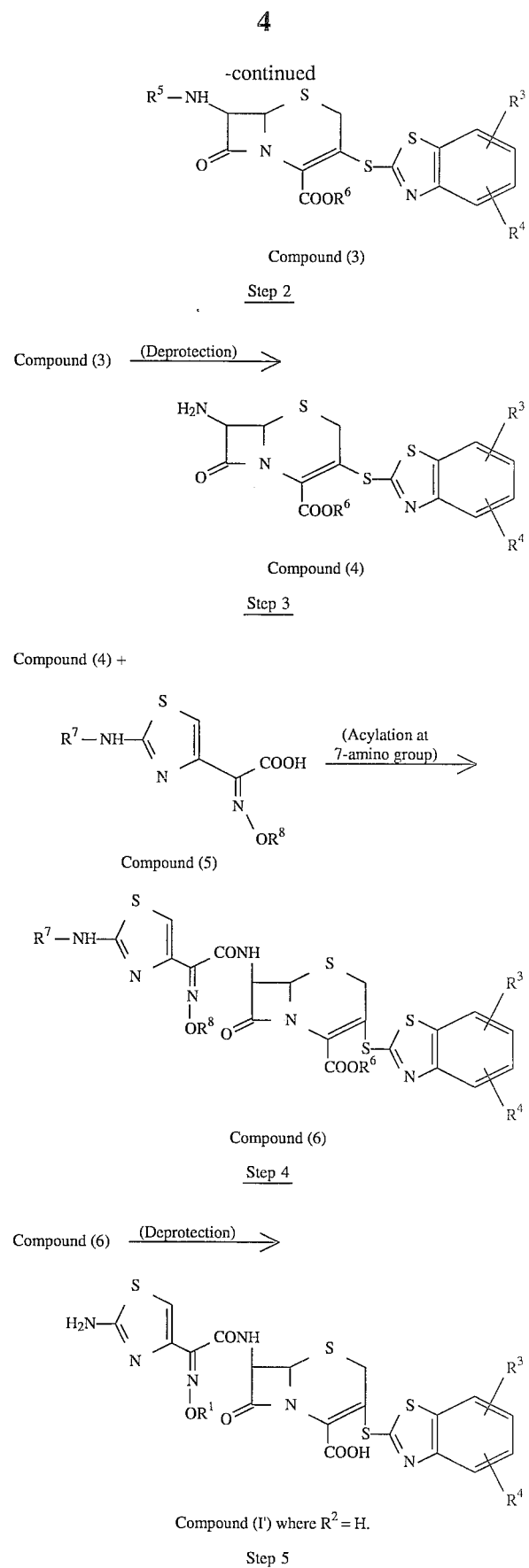

Compound (3)

Step 2

Compound (3) —(Deprotection)→

Compound (4)

Step 3

Compound (4) +

Compound (5)

(Acylation at 7-amino group)→

Compound (6)

Step 4

Compound (6) —(Deprotection)→

Compound (I') where $R^2$ = H.

Step 5

Compound (I') +

R²X¹  (Esterification) →

Compound (7)
(where R² = an ester-forming
group, X¹ = a halogen atom)

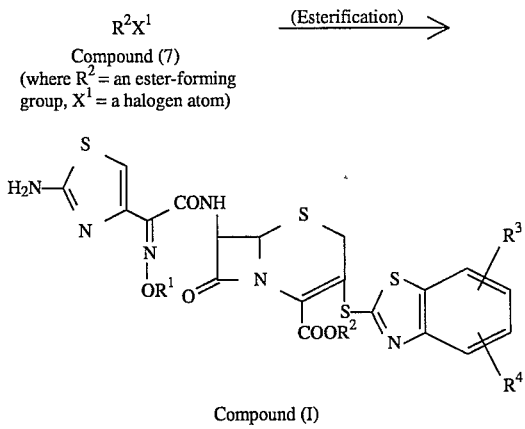

Compound (I)

In respect of each of Compounds (1) to (7) as well as Compound (I') and Compound (I) shown in the above reaction scheme, $R^1$, $R^2$, $R^3$ and $R^4$ described therein have respectively the same meanings as those defined for the compound of the general formula (I) according to this invention.

$R^5$ in the starting Compound (1) used in the step 1 of the above-mentioned production process (A) represents an amino-protecting group of acyl type such as a phenylacetyl group, phenoxyacetyl group, 2-thienylacetyl group, formyl group or t-butoxycarbonyl group, and $R^6$ represents an ester-forming group which is available as a carboxyl protecting group, such as a diphenylmethyl group, benzyl group, p-methoxybenzyl group, p-nitrobenzyl group, t-butyl group or 2,2,2-trichloroethyl group. X in the starting Compound (1) represents a leaving group which may be a halogen atom, diphenylphosphoryloxy group, methanesulfonyloxy group, p-toluenesulfonyloxy group or trifluoromethanesulfonyloxy group. Compound (5) used as the reaction reagent in the step 3, namely the protected aminothiazolylacetic acid has $R^7$ which represents an amino-protecting group such as trityl group, chloroacetyl group or formyl group. Further, $R^8$ in Compond (5) represents a lower alkyl group which is the same as $R^1$, or represents a protective group for the oxime group, such as trityl group. When this protective group ($R^8$) for the oxime group is eliminated in a subsequent step, the compound of the formula (I) where $R^1$ is hydrogen can be afforded.

Next, description will be made of the procedures for conducting the steps 1 to 5 depicted in the reaction scheme of the above-mentioned process (A).

In the above step 1, the starting Compound (1) is reacted with Compound (2), namely 2-mercaptobenzothiazole or its sodium salt having substituents $R^3$ and $R^4$ in an anhydrous organic solvent to effect the replacement reaction and to produce Compound (3). Preferable examples of the reaction solvent available for this reaction include chloroform, dichloromethane, tetrahydrofuran, N,N-dimethylformamide, acetonitrile and hexamethylphosphoric triamide. Moreover, it is preferred that this reaction is carried out in the presence of a base, depending upon the kinds of starting Compound (1) and the solvent used or others. In this case, usable examples of the base include organic bases such as triethylamine, tributylamine and N,N-diisopropylethylamine. Reaction temperature is preferably in a range of from −20° to 10° C. After completion of the reaction, the reaction solution is subjected to a post-treatment in a usual manner, and the resulting Compound (3) is, if necessary, purified by a column chromatography on silica gel or by crystallization.

In the step 2, Compound (3) is subjected to a deprotection reaction to remove the acyl group ($R^5$) as the amino-protecting group, thereby obtaining the 7-aminocephem compound (4). The procedure of this deprotection Can be effected in a usual manner for removing the amino-protecting group ($R^5$) present. In the case when $R^5$ is phenyiacetyl group, phenoxyacetyl group, 2-thienylacetyl group or the like, there can be utilized such a procedure which is often used for the removal of this kind of amino protecting group, i.e., such a procedure which comprises reacting Compound (3) first with phosphorus pentachloride and an organic base, and then with an alcohol. The resultant 7-aminocephem compound (4) can be purified and isolated by crystallization or a suitable chromatography, but it can also be directly used in the subsequent step 3 without being purified.

In the step 3, the amino group at the 7-position of the 7-aminocephem compound (4) is acylated with the compound (5), i.e., a desired aminothiazolylacetic acid or its active derivative to obtain Compound (6). This acylation reaction may be carried out in such a manner as used in the usual synthetic chemistry of a peptide. For example, the 7-aminocephem compound (4) is reacted with aminothiazolylacetic acid (5) or its active derivative in the presence of a variety of condensation agents to give Compound (6). Example of the condensation agent include dicyclohexylcarbodiimide, Viismeier reagent and phosphorus oxychloride. The condensation agent can be suitably selected from these examples in consideration of the reactivity and other factors of Compound (4), aminothiazolylacetic acid (5) or its active derivative to be used. The solvent is preferably dichloromethane, chloroform, N,N-dimethylformamide or tetrahydrofuran, and the reaction temperature is in the range of −20° C. to +50° C., preferably −20° C. to 0° C. After completion of the reaction, the resulting reaction solution is subjected to a usual post-treatment, and the resultant compound (6) is, if necessary, purified by a column chromatography on silica gel.

In the step 4, the remaining protective groups $R^6$, $R^7$ and $R^8$ of Compound (6) are removed by suitable deprotection reactions to afford a compound of the general formula (I) according to this invention where $R^2$ is a hydrogen atom, i.e., the Compound (I'). At this time, the deprotection reactions for the removal of the groups $R^6$, $R^7$ and $R^8$ can be carried out in a suitable order, so long as such reactions are performed in a usual manner for the removal of the protective groups $R^6$,$R^7$ and $R^8$. In a case when the removal of the groups $R^6$, $R^7$ and $R^8$ is to be carried out under acidic conditions, Compound (6) may be treated with trifluoroacetic acid, formic acid or hydrochloric acid. In the case when a part or all of the groups $R^6$, $R^7$ and $R^8$ are removed under reducing conditions, the compound (6) may be treated with a catalytic reduction with an optional catalyst or a reducing metal such as zinc. Furthermore, in such case when $R^7$ is chloroacetyl group, this group can be removed by reacting Compound (6) with a variety of thioamides. The compound (I') thus obtained can be crystallized and precipitated from its aqueous solution by adjusting the pH. In addition, the compound (I') can be purified and isolated by a chromatography using a nonionic macroporous resin or by a gel filtration using Sephadex.

In the step 5, such a compound is produced where $R^2$ in the compound (I) of this invention is an ester forming group which can be easily cleaved by an esterase enzyme existing in the digestive tracts. For this purpose, the compound (I')

obtained in the step 4 is esterified by reaction with Compound (7), namely an alcohol R²OH or its reactive derivative such as a halide derivative or an active ester in a known manner. In this esterification reaction, acetonitrile, N,N-dimethylformamide, N,N-dimethylacetamide or acetone is suitably used as the solvent, and the reaction temperature may be in a range of −40° C. to room temperature, preferably −20° C. to 0° C. The reaction can usually finish in a period of 1 hour or less, depending upon the amount of an esterifying agent to be used, the reaction temperature and others. After completion of the reaction, the resulting reaction solution is subjected to a usual post-treatment, and the resultant desired compound (I) is, if necessary, purified through a column chromatography on silica gel, precipitated or crystallized to isolate the desired product.

Example for the preparation of the cephalosporin derivative (I) of the present invention according to this production process (A) will be illustrated with reference to Example 1, Example 3 and Example 4 which will be given hereinafter.

In addition, the cephalosporin derivative of the formula (I) according to the present invention can also be prepared in accordance with such a production process (B) comprising the steps (a) to (e) depicted in the following reaction scheme.

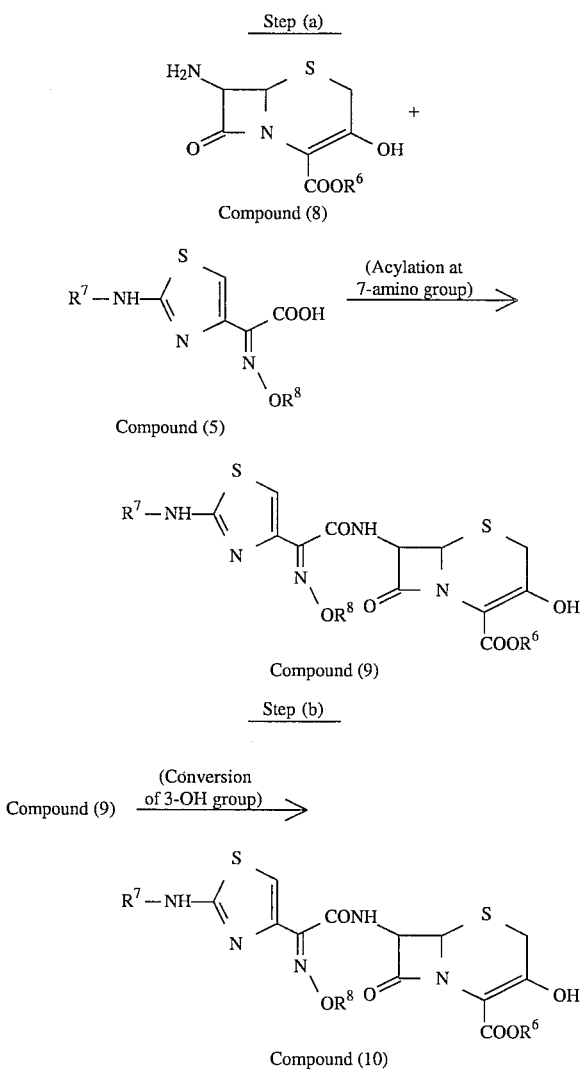

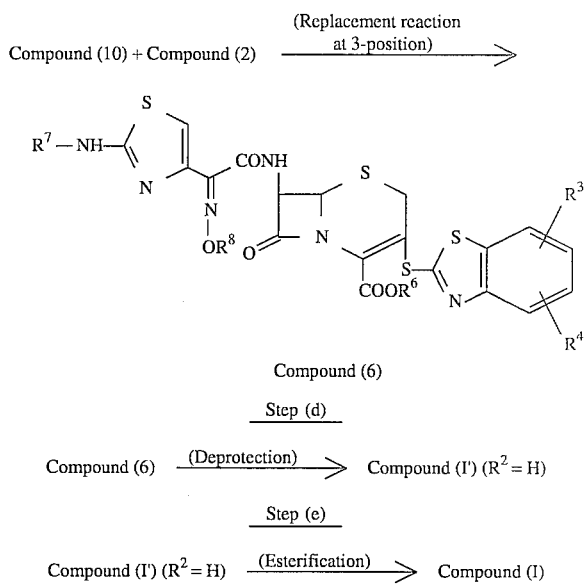

In the above reaction scheme shown for the step (a) to the step (e), $R^1$, $R^2$, $R^3$, $R^4$, $R^6$, $R^7$ and $R^8$ as well as X described therein have respectively the same meanings as those which are defined in the production process (A) given hereinbefore.

In the step (a) of the production process (B), the 3-hydroxycephem compound (8) used as the starting compound is reacted with a desired aminothiazolylacetic acid, namely Compound (5) or its derivative in the same manner as in the step 3 of the production process (A), so that the 7-amino group of Compound (8) is acylated and Compound (9) of enol form is thus synthesized. At this time, it is often preferred that the 3-hydroxyl group of Compound (8) has been protected with a hydroxyl-protecting group such as a silyl group, depending upon the sorts of the solvent, the reaction reagent used and other factors.

In the step (b), Compound (9) of the enol form is reacted with a variety of halogenating agents, an acid anhydride or an acid chloride in the presence of a base in an anhydrous organic solvent so as to convert the 3-hydroxyl group of Compound (9) into a leaving group X, thereby obtaining Compound (10). Suitable examples of the reaction solvent include chloroform, dichloromethane, tetrahydrofuran, dimethylformamide and acetonitrile. Furthermore, examples of the usable base include organic bases such as triethylamine, tributylamine and N,N-diisopropylethylamine. Reaction temperature is preferably in a range of from −60° C. to −10° C. After completion of the reaction, the resulting reaction solution is post treated in a usual way, and Compound (10) obtained is, if necessary, purified by a column chromatography on silica gel or by crystallization.

In the step (c), the leaving group (X) at the 3-position of Compound (10) is reacted with Compound (2) in the same manner as in the step 1 of the production process (A) to afford Compound (6).

In the step (d), Compound (6) is subjected to suitable deprotection reactions in the same manner as in the step 4 of the production process (A) thereby obtaining Compound (I') where $R^2$ is a hydrogen atom.

In the step (e), Compound (I') is esterified in the same manner as in the step 5 of the production process (A), to produce the compound (I) which is aimed at by this invention.

The cephalosporin derivative of the general formula (I) according to this invention has advantageous characteristics to exhibit a high antibacterial activity against various pathogenic bacteria and exhibit a capability to give and maintain a high concentration of the cephalosporin derivative in blood after its administration.

Next, the above-mentioned advantageous biological properties of the new cephalosporin compounds of this invention will be described with reference to their representative particular compounds.

TEST EXAMPLE 1

In this Test Example, the antibacterial activity of some exemplary compounds indicated below and chosen from amongst the compounds of the general formula (I) according to this invention is illustrated by determining their minimum growth inhibition concentrations to various bacteria as measured by a standard serial dilution method. In this case, the determination was carried out by inoculating $10^6$ CFU/ml of test bacteria to a culture medium N for sensitive disc (as prepared by Nissui Pharmaceutical Co., Ltd.), incubating the bacteria at 35° C. for 18 to 20 hours, and then evaluating the bacterial growth. Test compounds used are as follows:

Compound (A): 7-[(Z)-2-(2-aminothiazol-4-yl)-2methoxyiminoacetamido] -3-(benzothiazol-2-yl)thio-3-cephem-4-carboxylic acid Compound (B): 7-[(Z)-2-(2-aminothiazol-4-yl)-2hydroxyiminoacetamido] -3-(benzothiazol-2-yl)thio-3-cephem-4-carboxylic acid Compound (C): 7-[(Z)-2-(2-aminothiazol-4-yl)-2carboxymethoxyiminoacetamido] -3-(benzothiazol-2-yl)thio 3-cephem-4-carboxylic acid The measured values of the minimum growth inhibition concentrations (μmg/ml) of the above-mentioned compounds A, B and C are shown in Table 1.

TABLE 1

| | Minimum growth inhibition concentration (μg/ml) | | |
|---|---|---|---|
| Test bacteria strain | Compound A | Compound B | Compound C |
| Staphylococcus aureus 209P JC-1 | 0.39 | 0.20 | 3.13 |
| Staphylococcus aureus M133 (*) | 3.13 | 1.56 | 12.5 |
| Staphylococcus aureus M126 (*) | 6.25 | 3.13 | 50 |
| Staphylococcus epidermidis ATCC14990 | 0.20 | 0.20 | 1.56 |
| Escherichia coli NIHJ JC-2 | 3.13 | 25 | 3.13 |
| Klebsiella pneumoniae PCI602 | 3.13 | 25 | 3.13 |
| Proteus vulgaris GN76 | 3.13 | 100 | 0.10 |
| Marganella morganii 1510/S-1 | 0.78 | 3.13 | 0.78 |

Note: (*) means methicillin-resistant Staphylococus aureus.

TEST EXAMPLE 2

In this Test Example, it is demonstrated that the undermentioned test compounds which are representative examples of the new compounds of this invention can give and maintain their high concentrations in blood upon their subcutaneous injection. Test compounds used are as follows:

Compound (A): 7-[(Z)-2-(2-aminothiazol-4-yl)-2methoxyiminoacetamido] -3-(benzothiazol-2-yl)thio-3 cephem-4-carboxylic acid Compound (C): 7-[(Z)-2-(2-aminothiazol-4-yl)-2carboxymethoxyiminoacetamido] -3-(benzothiazol-2-yl)thio 3-cephem-4-carboxylic acid The test procedure used was as follows. That is, 5 mice of ICR strain (male, 4-weeks-aged, 1 mouse in each group/at the time of collection of blood samples) were used as test animal and 0.5 mg of each test compound dissolved in 0.2 ml of a purified water sterilized for injection was subcutaneously injected to each mouse. Blood samples were collected from each mouse 5 minutes, 15 minutes, 30 minutes, 1 hour and 2 hours after the aministration of test compound. Each blood sample as collected was post-treated in a usual manner and the concentration of the cephem compound in the serum was then quantitatively determined by the use of HPLC (High Performance Liquid Chromatography). A half-life value and AUC which were pharmacokinetic parameters were calculated by the Gauss-Newton method.

The determined maximum concentrations and half-life values of the tested Compounds A and C in blood are set forth in Table 2. AUC means "Area under the plasma concentration-time curve".

TEST EXAMPLE 3

TABLE 2

| Measurement Item | Compound A | Compound C |
|---|---|---|
| Maximum concentration in blood (μg/ml) | 51.6 | 80.8 |
| Half-life value (hr) | 0.70 | 0.92 |
| AUC (μg · hr/ml) | 62.5 | 131.3 |

In this test example, it is demonstrated that the undermentioned test compound which is representative of the compounds of this invention can give and maintain their high concentrations in blood upon the oral administration.

Test compound used is as follows:

Compound (D): Pivaloyloxymethyl 7-[(Z)-2-(2-aminothiazol 4-yl)-2-methoxyiminoacetamido]-3-(benzothiazol-2-yl)thio 3-cephem-4-carboxylate The test procedure used was as follows. That is, 6 mice of ICR strain (male, 4-weeks-aged, 1 mouse in each group/at the time of collection of blood-samples) were used as test animal, and 0.5 mg of the test compound suspended in 1 ml of a 0.2% aqueous CMC solution was orally administered to each mouse. Blood samples were collected from each mouse 5 minutes, 15 minutes, 30 minutes, 1 hour, 2 hours and 4 hours after the oral administration of the test compound. Each blood sample as collected was post-treated in a usual manner and the concentration of the cephem compound in the serum was determined by the use of HPLC in term of the concentration of the cephem compound in the form of its free acid. A half-life value and AUC which were the pharmacokinetic parameters were calculated by the Gauss-Newton method.

The determined maximum concentration and the half-life value of the test Compound D in blood are set forth in Table 3 together with the AUC value so calculated that the AUC value was represented in term of the concentration of the free acid compound as formed by the hydrolysis of Compound D in the ester form.

TABLE 3

| Measurement Item | Compound D |
|---|---|
| Maximum concentration in blood | 4.0 |

TABLE 3-continued

| Measurement Item | Compound D |
| --- | --- |
| (µg/ml) | |
| Half-life value (hr) | 1.80 |
| AUC (µg · hr/ml) | 20.6 |

As described above, the cephalosporin derivative of the general formula (I) according to this invention exhibits high antibacterial activity and maintains a high concentration of the active compound in blood and also has an excellent oral absorbability. Thus, the new cephalosporin derivative of this invention is very useful as a therapeutic agent for treatment of bacterial infections of various pathogenic bacteria. The new compound of this invention having the formula (I) may be formulated into various preparations suitable for administration.

According to a further aspect of this invention, therefore, there is provided a pharmaceutical, antibacterial composition comprising an antibacterially effective amount of a compound of the general formula (I) given hereinbefore or a pharmaceutically acceptable salt or ester thereof as active ingredient, in combination with a pharmaceutically acceptable carrier for the active ingredient.

The pharmaceutically acceptable carrier as mixed with the active ingredient compound may be an ordinary solid or liquid one, either organic or inorganic, for example, starch, sugar, water and aqueous ethanol, which may be chosen appropriately depending on whether the pharmaceutical formulation as prepared is to be administered orally or non-orally or applied externally. The pharmaceutical composition of this invention may be of any conventional formulation form such as capsules, tablets, sugar-coated pills, ointment, suppository, solution, suspension and emulsion. Other conventional additives, including adjuvant, stabilizing agent, wetting agent, emulsifying agent, buffer solution may also be incorporated into the pharmaceutical composition of this invention containing the compound of the formula (I) as the active ingredient.

The cephalosporin derivative of the general formula (I) according to this invention can safely be administered to mammals because it is of low toxicity. It has been demonstrated that intravenous administration of 7-[(Z)-2-(2-aminothiazol-4-yl)-2-methoxyiminoacetamido] 3-(benzothiazol-2-yl)thio-3-cephem-4-carboxylic acid gives an $LD_{50}$ value of 1–1.5 g/kg in mice. This specific compound in its pivaloylmethyl ester may have a similar $LD_{50}$ value. The new cephalosporin derivative of this invention may be administered orally at a unit dose of 100 mg to 250 mg to an adult human patient four times a day, for a guideline. However, precise dosage of the new cephalosporin derivative of this invention is determinable through preliminary routine experiments, depending on the body weight, ages, sex and other various parameters of patients as well as the nature of the bacterial infections to be treated, and so on.

Now, this invention will be illustrated with reference to the following Examples.

EXAMPLE 1

(a) Diphenylmethyl 7-phenylacetamido-3-(benzothiazol 2,yl)thio-3-cephem-4-carboxylate 2.98 g of diphenylmethyl 7-phenylacetamido-3-trifluoromethylsulfonyloxy-3-cephem-4-carboxylate were suspended in 30 ml of methylene chloride and the resulting suspension was cooled with ice. Next, 893 mg of a sodium salt of 2-mercaptobenzothiazol were added to said suspension and the reaction was then carried out for 5 hours under ice-cooling (to effect the reaction for the replacement at the 3-position of the starting cephem compound). After the resulting reaction solution was filtered, 150 ml of an aqueous saturated solution of sodium chloride were added to the filtrate which was then extracted with 150 ml of ethyl acetate. Afterward, the resultant organic layer (the extract) was washed with aqueous saturated sodium chloride solution and then dried over anhydrous magnesium sulfate. The dried organic solution obtained was distilled under reduced pressure to remove the solvents, and the resultant residue was then purified by a column chromatography on 200 g of silica gel (as developed with mixed solvents of toluene and ethyl acetate at ratio of 6:1 by volume) to collect a fraction containing the desired compound. After this fraction was distilled under reduced pressure to remove the solvent, the residue was crystallized from ethyl acetate-diisopropyl ether (1:10) to yield 1.44 g of the titled compound as white crystals (yield, 47%)

| NMR (CDCl$_3$) δ (ppm); | |
| --- | --- |
| 3.56 | (1H, d, J=18Hz) |
| 3.64 | (2H, ABq, J=17Hz) |
| 3.86 | (1H, d, J=18Hz) |
| 5.07 | (1H, d, J=5Hz) |
| 5.91 | (1H, dd, J=5, 9Hz) |
| 6.13 | (1H, d, J=9Hz) |
| 6.97 | (1H, s) |
| 7.20–7.50 | (17H, m) |
| 7.78 | (1H, d, J=7Hz) |
| 7.95 | (1H, d, J=7Hz) |

(b) diphenylmethyl 7-[(Z)-2-(2-tritylaminothiazol-4-yl)-2-methoxyiminoacetamido]-3-(benzothiazol-cephem-4-carboxylat 557 mg of diphenylmethyl 7-phenylacetamido-3-(benzothiazol-2-yl)thio-3-cephem-4-carboxylate were dissolved in 6 ml of methylene chloride, and the resulting solution was then cooled to −15° C. Afterward, to the cooled solution were added 0.16 ml of pyridine and 268 mg of phosphorus pentachloride, followed by stirring the resultant mixture at −5° C. for 1 hour and 30 minutes. Next, the mixture was cooled to −20° C., and 2.1 ml of methanol were then added thereto. The resulting solution was stirred again at −5° C. for 3 hours to continue the reaction (for the removal of the 7-phenylacetyl group). Thereafter, 6 ml of water were added to the reaction solution which was then further stirred at the same temperature for 1 hour, followed by separation into the aqueous and organic layers. 6 ml of water were added to the resultant organic layer which was then adjusted to pH 7 with an aqueous saturated solution of sodium hydrogen carbonate. After separation from the aqueous layer, the collected organic layer was dried over anhydrous magnesium sulfate. The dried organic solution obtained was distilled under reduced pressure to remove the solvent therefrom, and the resultant residue was then purified by a column chromatography on 35 g of silica gel (as developed with mixed solvents of toluene and ethyl acetate at ratio of 1:1 by volume) to give diphenylmethyl 7-amino-3-(benzothiazol-2-yl)thio-3-cephem-4-carboxylate as white crystals.

This cephem compound was dissolved in 6 ml of methylene chloride and the resulting solution was cooled to −20° C., followed by addition of 380 mg of (Z)-2( 2-tritylaminothiazol-4-yl)-2-methoxyiminoacetic acid, 0.25 ml of pyridine and 0.12 ml of phosphorus oxychloride thereto. Afterward, the resulting mixture was stirred at −20° C. for 10 minutes to perform the acylation reaction at the 7-amino group of the cephem compound. 6 ml of water were added to the reaction solution as formed, which was then stirred at room temperature for 1 hour and subsequently separated into the aqueous and organic layers. The organic layer was dried over anhydrous magnesium sulfate, followed by distillation under reduced pressure to remove the solvents therefrom. The resultant residue was then purified by a column chromatography on 35 g of silica gel (as developed with mixed solvents of toluene and ethyl acetate, 3:1) to give 430 mg of the titled compound (yield, 52%).

| NMR (CDCl$_3$) δ (ppm); | |
| --- | --- |
| 3.55 | (1H, d, J=18Hz) |
| 3.90 | (1H, d, J=18Hz) |
| 4.06 | (3H, s) |
| 5.17 | (1H, d, J=5Hz) |
| 6.00 | (1H, dd, J=5, 9Hz) |
| 6.73 | (1H, s) |
| 6.84 | (1H, d, J=9Hz) |
| 6.79 | (1H, s) |
| 7.15~7.50 | (27H, m) |
| 7.78 | (1H, d, J=9Hz) |
| 7.95 | (1H, d, J=9Hz) |

(c) 7-[(Z)-2-(2-aminothiazol-4-yl)-2-methoxy-iminoacetamido] 3-3-(benzothiazol-2-yl)thio-3-cephem-4-carboxylic acid 430 mg of diphenylmethyl 7-[(Z)-2-(2-tritylamino-thiazol-4-yl)-2-methoxyiminoacetamido 3-2-yl)thio-3-cephem-4-ca of anisole, and 4.3 ml of trifluoroacetic acid were then added to the resulting solution under ice-cooling.

Afterward, the mixture as obtained was stirred under the ice-cooling for 30 minutes to effect the reaction (for the removal of the trityl group and diphenylmethyl group). The resulting reaction solution was then added dropwise to 22 ml of diisopropyl ether, and the precipitate so deposited was collected by filtration and dried. The dried solid was suspended in 3 ml of distilled water, and the suspension obtained was then adjusted to pH 7 with aqueous saturated sodium hydrogen carbonate. Subsequently, the resulting solution was purified by mixing with 30 ml of a macroporous resin "Diaion HP-20", and the so purified solution was then freeze-dried to afford 115 mg of a sodium salt of the above titled compound (yield, 45%).

| NMR (DMSO-d$_6$) δ (ppm); | |
| --- | --- |
| 3.40 | (1H, d, J=17Hz) |
| 3.86 | (3H, s) |
| 3.94 | (1H, d, J=17Hz) |
| 5.18 | (1H, d, J=5Hz) |
| 5.70 | (1H, dd, J=5, 9Hz) |
| 6.73 | (1H, s) |
| 7.16 | (2H, s) |
| 7.32 | (1H, t, J=8Hz) |
| 7.42 | (1H, t, J=8Hz) |
| 7.80 | (1H, d, J=8Hz) |
| 7.92 | (1H, d, J=8Hz) |
| 9.71 | (1H, d, J=9Hz) |

EXAMPLE 2

Pivaloyloxymethyl 7-[(Z)-2-(2-aminothiazol-4-yl)-2methoximinoacetamido] -3-(benzothiazol-2-yl)thio-3-cephem-4-carboxylate 83 mg of sodium 7-[(Z)-2-(2-aminothiazol-4-yl)-2meth-oxyiminoacetamido] -3-(benzothiazol-2-yl)thio-3-cephem 4-carboxylate as obtained in Example 1 above were dissolved in 2 ml of N,N-dimetylformamide and the resulting solution was cooled to −20° C. Next, 70 mg of iodomethyl pivalate were added thereto, and the mixture obtained was stirred at −20° C. for 30 minutes to effect the esterification of the cephem compound. Afterward, 5 ml of water were added to the resulting reaction solution, which was then extracted with ethyl acetate. The resultant organic layer (the extract) was washed with an aqueous sodium chloride solution and dried over anhydrous magnesium sulfate. Afterward, the dried organic solution was distilled under reduced pressure to remove the solvent, and the resultant residue was then purified by a column chromatography on 30 g of silica gel (as developed with mixed solvents of toluene and ethyl acetate, 1:2). The eluate fraction containing the desired cephem compound was distilled under reduced pressure to remove the solvent therefrom, and the resultant residue was crystallized from mixed solvents of ethyl acetate and diisopropyl ether (1:10) to afford 58 mg of the titled compound (yield, 61%).

| NMR (DMSO-d$_6$) δ (ppm); | |
| --- | --- |
| 1.19 | (9H, s) |
| 3.59 | (1H, d, J=18Hz) |
| 3.96 | (1H, d, J=18Hz) |
| 4.04 | (3H, s) |
| 5.20 | (1H, d, J=5Hz) |
| 5.21 | (2H, s) |
| 5.89 | (1H, d, J=5Hz) |
| 5.96 | (1H, s, J=5Hz) |
| 6.06 | (1H, dd, J=5, 9Hz) |
| 6.91 | (1H, s) |
| 7.30 | (1H, d, J=9Hz) |
| 7.41 | (1H, t, J=8Hz) |
| 7.49 | (1H, t, J=8Hz) |
| 7.82 | (1H, d, J=8Hz) |
| 7.97 | (1H, d, J=8Hz) |

EXAMPLE 3

(a) Diphenylmethyl 7-[(Z)-2-(2-tritylaminothiazol-4-yl) 2-trityloxyiminoacetamido]-3-(benzothiazol-2-yl)thio-3-cephem-4-carboxylate 350 mg of diphenylmethyl 7-amino-3-(benzothiazol-2-yl)thio-3-cephem-4-carboxylate as synthesized in the same manner as in Example 1 (b) above were dissolved in ml of methylene chloride, and to the solution obtained were added 531 mg of (Z)-2-(2-tritylaminothiazol-4-yl)-trityloxyiminoacetic acid, 0.21 ml of pyridine and 74 µl of phosphorus oxychloride. Next, the acylation reaction and the post-treatment of the reaction solution were carried out in the same way as in Example 1 (b), and the resultant residue was then purified by a column chromatography on 35 g of silica gel (as developed with mixed solvents of toluene and ethyl acetate, 10:1) to obtain 566 mg of the titled compound (yield, 73%).

| NMR (CDCl$_3$) δ (ppm); | |
| --- | --- |
| 3.36 | (1H, d, J=18Hz) |
| 3.81 | (1H, d, J=18Hz) |
| 5.18 | (1H, d, J=5Hz) |
| 6.12 | (1H, dd, J=5, 9Hz) |
| 6.43 | (1H, s) |
| 7.00 | (1H, s) |

| NMR (CDCl₃) δ (ppm); | |
|---|---|
| 7.20–7.50 | (42H, m) |
| 7.74 | (1H, d, J=8Hz) |
| 7.93 | (1H, d, J=8Hz) |

(b) 7-[(Z)-2-(2-aminothiazol-4-yl)-2-hydroxyiminoacetamido] -3-(benzothiazol-2-yl)thio-3-cephem-4-carboxylic acid 566 mg of diphenylmethyl 7-[(Z)-2-(2-tritylamino-thiazol-4-yl)-2-trityloxyiminoacetamido]-3-(b 2-yl)thio-3-cephem-4-carboxylate, 2.8 ml of anisole and 5.6 ml of trifluoroacetic acid were reacted with each other in the same manner as in Example 1 (c) to effect the removal of the trityl groups and diphenylmethyl group for the deprotection purpose. Further, the reaction solution so obtained was subjected to a similar post treatment to afford 33 mg of a sodium salt of the titled compound (yield, 12%).

| NMR (DMSO-d₆) δ (ppm); | |
|---|---|
| 3.32 | (1H, d, J=17Hz) |
| 3.92 | (1H, d, J=17Hz) |
| 5.18 | (1H, d, J=5Hz) |
| 5.73 | (1H, dd, J=5, 9Hz) |
| 6.65 | (1H, s) |
| 7.07 | (2H, s) |
| 7.31 | (1H, t, J=9Hz) |
| 7.41 | (1H, t, J=9Hz) |
| 7.80 | (1H, d, J=9Hz) |
| 7.92 | (1H, d, J=9Hz) |
| 9.55 | (1H, d, J=9Hz) |
| 11.29 | (1H, s) |

EXAMPLE 4

(a) Diphenylmethyl 7-[(Z)-2-(2-tritylaminothiazol-4-yl) 2-diphenylmethoxycarbonylmethoxyiminoacetamido]- 3-(benzothiazol-2-yl)thio-3-cephem-4-carboxylate 165 mg of diphenylmethyl 7-amino-3-(benzothiazol-2-yl)thio-3-cephem-4-carboxylate as synthesized in the same manner as in Example 1 (b) above were dissolved in 4 ml of methylene chloride, and to the resulting solution were added 243 mg of (Z)-2-(2-tritylaminothiazol-4-yl)-2-diphenylmethoxycarbonylmethoxyiminoacetic acid, 0.10 of pyridine and 35 μl of phosphorus oxychloride. Next, the acylation reaction and the post-treatment of the reaction solution were carried out in the same manner as in Example 1 (b), and the resultant residue was then purified through a column chromatography on 30 g of silica gel (as developed with mixed solvents of toluene and ethyl acetate, 10:1) to afford 260 mg of the titled compound (yield, 73%).

| NMR (CDCl₃) δ (ppm); | |
|---|---|
| 3.29 | (1H, d, J=18Hz) |
| 3.77 | (1H, d, J=18Hz) |
| 4.87 | (1H, d, J=17Hz) |
| 5.00 | (1H, d, J=17Hz) |
| 5.06 | (1H, d, J=5Hz) |
| 5.94 | (1H, dd, J=5, 9Hz) |
| 6.77 | (1H, s) |
| 6.94 | (1H, s) |
| 6.98 | (1H, s) |
| 7.10–7.50 | (37H, m) |
| 7.73 | (1H, d, J=8Hz) |
| 7.94 | (1H, d, J=8Hz) |
| 8.09 | (1H, d, J=9Hz) |

(b) 7-[(Z)-2-(2-aminothiazol-4-yl)-2-carboxymethoxyiminoacetamido] -3-(benzothiazol-2-yl) thio-3-cephem-4carboxylic acid 260 mg of diphenylmethyl 7-[(Z)-2-(2-trityl-aminothiazol-4-yl)-2-diphenylmethoxycarbonylmethoxyiminoac -3-(benzothiazol-2-yl)thio-3-cephem-4carboxylate, 1.3 ml of anisole and 2.6 ml of trifluoroacetic acid were reacted together in the same manner as in Example 1 (c) to bring about the removal of the trityl group and diphenylmethyl groups. Further, the resulting reaction solution was subjected to the post-treatment in the same way as in Example 1 (c) to obtain 62 mg of a sodium salt of the above titled compound (yield, 43%).

| NMR (DMSO-d₆) δ (ppm); | |
|---|---|
| 3.30 | (1H, d, J=17Hz) |
| 3.88 | (1H, d, J=17Hz) |
| 4.32 | (2H, s) |
| 5.19 | (1H, d, J=5Hz) |
| 5.65 | (1H, dd, J=5, 9Hz) |
| 6.86 | (1H, s) |
| 7.15 | (2H, s) |
| 7.30 | (1H, t, J=8Hz) |
| 7.40 | (1H, t, J=8Hz) |
| 7.79 | (1H, d, J=8Hz) |
| 8.00 | (1H, d, J=8Hz) |
| 12.23 | (1H, d, J=9Hz) |

We claim:

1. 7-[(Z)-2-(2-Aminothiazol-4-yl)-2-carbOxYmethoximinoacetamido] -3-(benzothiazol-2-yl)thio-3-cephem-4-carboxylic acid, and a pharmaceutically acceptable salt or ester thereof.

2. An ester of the cephem compound according to claim 1 which is an ester with an ester-forming group easily cleavable by an esterase present in the digestive tracts, said ester-forming group being selected from pivaloyloxymethyl group, acetoxymethyl group, 1-acetoxyethyl group, 1-(ethoxycarbonyloxy)ethyl group, 1-(isopropoxycarbonyloxy)ethyl group and (5-methyl-1,3-dioxolen-4-yl)methyl group.

3. A pharmaceutical, antibacterial composition which comprises an antibacterially effective amount of the cephem compound of claim 1 or a pharmaceutically acceptable salt or ester thereof, as the active ingredient, in combination with a pharmaceutically acceptable carrier for the active ingredient.

* * * * *

UNITED STATES PATENT AND TRADEMARK OFFICE
CERTIFICATE OF CORRECTION

PATENT NO. : 5,461,044
DATED : October 24, 1995
INVENTOR(S) : Masaki Tsushima, et al.

It is certified that error appears in the above-identified patent and that said Letters Patent is hereby corrected as shown below:

In Claim 1, Line 1, delete "carb0xYmethoximinoacetamido" and insert therefor -- carboxymethoximinoacetamido --.

Signed and Sealed this

Twenty-second Day of April, 1997

Attest:

BRUCE LEHMAN

Attesting Officer

Commissioner of Patents and Trademarks